United States Patent [19]

Ong et al.

[11] Patent Number: 4,769,472
[45] Date of Patent: Sep. 6, 1988

[54] INTERMEDIATE THIENO-ISOXAZOLES AND -PYRAZOLES AND 5-BENZOYL-4-BROMOTHIOPHENES

[75] Inventors: Helen H. Ong, Whippany; Christine M. Yasenchak, Somerville, both of N.J.

[73] Assignee: Hoechst-Roussel Pharmaceuticals, Inc., Somerville, N.J.

[21] Appl. No.: 125,108

[22] Filed: Nov. 25, 1987

Related U.S. Application Data

[62] Division of Ser. No. 791,019, Oct. 24, 1985, Pat. No. 4,728,651.

[51] Int. Cl.$^4$ .................. C07D 498/04; C07D 333/28
[52] U.S. Cl. .................. 548/242; 548/370; 549/72; 549/75
[58] Field of Search .................. 548/242, 370; 549/72, 549/75

[56] References Cited

U.S. PATENT DOCUMENTS 4,387,100 6/1983 Machin .................. 514/406
4,409,231 10/1983 Stenzel et al. .................. 514/406

Primary Examiner—Alan L. Rotman
Assistant Examiner—Kurt G. Briscoe
Attorney, Agent, or Firm—Tatsuya Ikeda

[57] ABSTRACT

There are described compounds of the formula

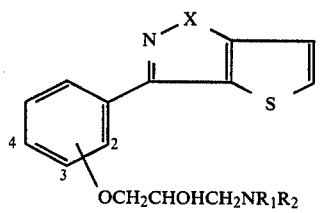

OCH$_2$CHOHCH$_2$NR$_1$R$_2$ where X is O or NR, R being hydrogen or loweralkyl; R$_1$ is hydrogen; and R$_2$ is loweralkyl, arylloweralkyl, aryloxyloweralkyl or loweralkyl substituted with

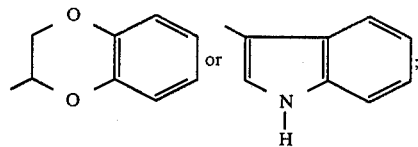

or alternatively—NR$_1$R$_2$ taken together is

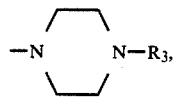

R$_3$ being arylloweralkyl or a pharmaceutically acceptable acid addition salt thereof, which are useful as ocular or systemic antihypertensive agents.

There are also described intermediate compounds having the formula

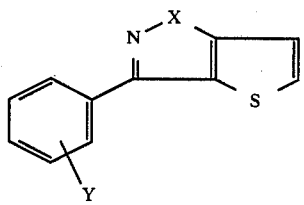

where X is oxygen or NR, R being hydrogen or loweralkyl; and Y is —OCH$_3$, —OH or

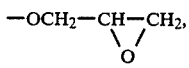

as well as intermediate compounds of the formula

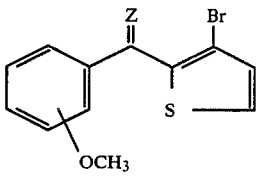

where Z is oxygen, NOH or NNHR$_4$, R$_4$ being hydrogen or loweralkyl.

58 Claims, No Drawings

INTERMEDIATE THIENO-ISOXAZOLES AND -PYRAZOLES AND 5-BENZOYL-4-BROMOTHIOPHENES

This is a division, of application Ser. No. 791,019 filed Oct. 24, 1985, now U.S. Pat. No. 4,728,651.

This invention relates to novel compounds of the formula (I)

[structure with OCH₂CHOHCH₂NR₁R₂ substituent]

where X is O or NR, R being hydrogen or loweralkyl; R₁ is hydrogen; and R₂ is loweralkyl, arylloweralkyl, aryloxyloweralkyl or loweralkyl substituted with

[benzodioxole or indole substituent structures]

or alternatively —NR₁R₂ taken together is

[piperazine structure with —N N—R₃]

R₃ being arylloweralkyl or a pharmaceutically acceptable acid addition salt thereof, which are useful as ocular or systemic antihypertensive agents; to antihypertensive composition comprising such compounds; to a method of treating a patient in need of blood pressure or ocular pressure lowering using such antihypertensive compositions; and to methods of synthesizing such compounds.

This invention also relates to novel compounds of formula (II) through (V) below where Y is —OCH₃, —OH or

—CH₂CH——CH₂,
    \O/ and R₄ is hydrogen or loweralkyl which are useful as intermediates for synthesizing compounds I.

(II) [structure with O, Br, OCH₃]

(III) [structure with OH, N, Br, OCH₃]

(IV) [structure with NHR₄, N, Br, OCH₃]

(V) [structure with N-Y, Y]

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall means a phenyl group having 0, 1, 2 or 3 substituents each of which being independently loweralkyl, loweralkoxy, hydroxy, halogen or CF₃.

The compounds of this invention are prepared by following one or more of the steps described below. Throughout the description of the synthetic steps, the definitions of X, Y, R, R₁, R₂, R₃ and R₄ are as given above unless otherwise stated or indicated.

STEP A

Compound II is prepared by reacting methoxybenzoyl chloride with 3-bromo-2-lithiothiophene.

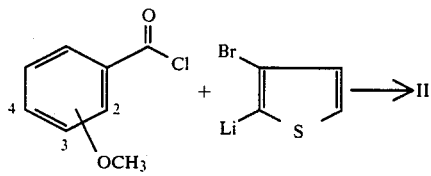

Typically, said reaction is conducted by first preparing the lithio compound by adding a solution of phenyllithium in a suitable solvent such as ether to a stirred solution of 3-bromothiophene in a suitable solvent such as ether and continuing the reaction at about 0°–30° C. and thereafter adding the resultant solution to a solution of methoxybenzoyl chloride in a suitable solvent such as tetrahydrofuran at a temperature between about −70° C. and −60° C. and continuing the reaction at this temperature (optionally with a gradual increase of temperature up to about ambient temperature).

STEP B

Compound II is reacted with hydroxylamine to afford the aforementioned oxime compound of formula III.

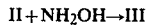

Said oxime formation reaction is typically conducted by stirring a mixture comprising compound II, hydroxylamine hydrochloride and a suitable solvent such as pyridine at a temperature of about 25°–100° C.

STEP C

Compound II is reacted with hydrazine to afford the aforementioned hydrazone compound of formula IVa.

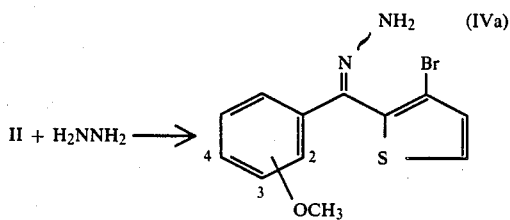

Typically said reaction is conducted by stirring a mixture comprising compound II, hydrazine hydrate and a suitable solvent such as ethylene glycol at a temperature of about 120°–140° C.

STEP D

Compound III is cyclized to afford a compound of formula VI below.

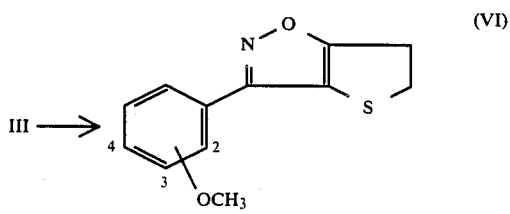

Typically, said cyclization is conducted in the presence of alkali metal hydroxide (e.g. potassium hydroxide), cuprous halide (e.g. cuprous chloride), water and a suitable medium such as diethylene glycol (2-ethoxyethanol) at a temperature of about 100°–120° C.

STEP E

Compound IVa is cyclized to afford a compound of the formula VII below.

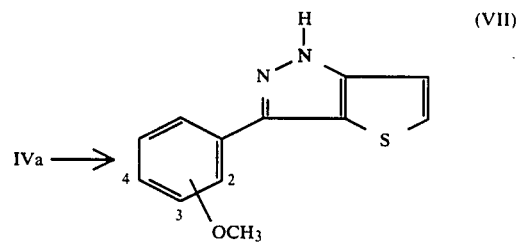

Typically said cyclization is conducted in the presence of alkali metal hydroxide (e.g. potassium hydroxide), cuprous halide (e.g. cuprous chloride), water and a suitable medium such as diethylene glycol at a temperature of about 70°–120°.

STEP F

Compound II is reacted with a loweralkyl-substituted hydrazine of formula H₂NNHR₄ where R₄ is loweralkyl to afford a compound of formula VIII below via the hydrazone intermediate indicated below.

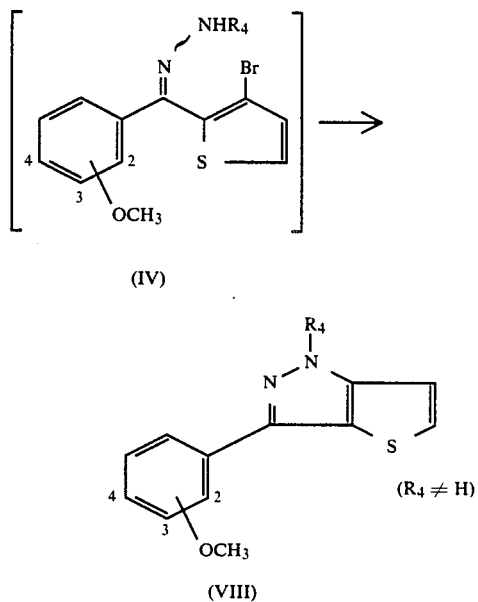

Typically said reaction is conducted in a suitable solvent such as ethylene glycol at a temperature of about 100°–130° C. If it is desired to obtain a hydrazone intermediate compound depicted above, a somewhat milder condition than above should be used.

STEP G

The methoxy compound for formula Va below, which is obtained from STEP D, E or F, is converted to the corresponding phenol of formula Vb below.

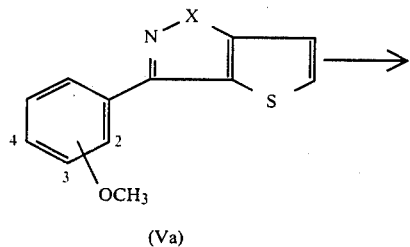

(Va)

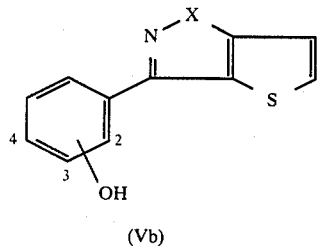

(Vb)

Said cleavage reaction is typically conducted by reacting compound Va with boron tribromide in a suitable solvent such as dichloromethane at about ambient temperature and thereafter adding water to the reaction product, or alternatively by reacting compound Va with pyridine hydrochloride at a temperature of about 130°–150° C.

STEP H

Compound Vb is reacted with epibromohydrin or epichlorohydrin to afford the epoxy compound of formula Vc below.

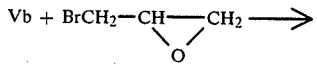

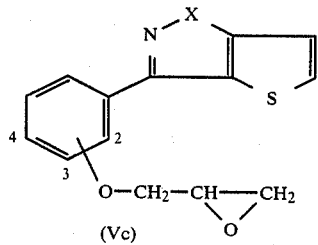

(Vc)

Typically said reaction is conducted in the presence of an acid scavenger such as potassium carbonate and a suitable medium such as dimethylformamide or acetonitrile at a temperature of about 70°–80° C.

STEP I

Compound Vc is used to prepare various compounds of formula I by reacting it with various amines of the general formula $HNR_1R_2$ where $R_1$ and $R_2$ are as defined earlier.

Said reaction is typically conducted in the presence of a suitable solvent such as ethyl acetate or ethanol at a temperature of about 70°–80° C., preferably under a reflux condition.

The thieno-isoxazoles and -pyrazoles of formula I of the present invention are useful in the treatment of elevated intraocular pressure by virtue of their ability to reduce intraocular pressure as determined by the method described by J. Caprioli, et al., Invest. Ophthalmol. Vis. Sci., 25, 268 (1984). The results of the determination expressed as percent decrease of outflow pressure is presented in Table I.

TABLE I

| Compound | Concentration % | % Decrease in outflow pressure |
| --- | --- | --- |
| 1-[(1,1-Dimethylethyl)amino]-3-[2-(thieno[2,3-d]isoxazol-3-yl)phenoxy]-2-propanol maleate | 2.0 | 36 |
| 1-[(1-Methylethyl)amino]-3-[(3-thieno[2,3-d]isoxazol-3-yl)-phenoxy]-2-propanol | 2.0<br>1.0 | 45<br>25 |
| 1-[[2-(3,4-Dimethoxyphenyl)-ethyl]amino]-3-[2-(thieno-[2,3-d]isoxazol-3-yl)phenoxy]-2-propanol | 4.0 | 38 |
| 1-[(1,1-Dimethylethyl)amino]-3-[2-(1-methyl-1H—thieno-[3,2-c]pyrazol-3-yl)phenoxy]-2-propanol | 2.0<br>0.5 | 51<br>27 |

Intraocular pressure reduction is achieved when the compounds of this invention are administered to a subject requiring such treatment as an effective topical dose of a 0.01 to 3.0% solution or suspension. A particularly effective amount is about 3 drops of a 1% preparation per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The thieno-isoxazoles and -pyrazoles of formula I of the present invention are also useful as systemic antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure is measured on the third day following administration. The antihypertensive activity is expressed as mm Hg decrease in systolic blood pressure. Some of the compounds of this invention were tested according to this spontaneous hypertensive rat (SHR) test and were found to produce the results shown in Table II. The dose is indicated as mg of the compound per kg body weight by oral (PO) administration.

TABLE II

| ANTIHYPERTENSIVE ACTIVITY | | |
| --- | --- | --- |
| Compound | SHR mmHg | Dose mg/kg, PO |
| 1-[[2-(3,4-Dimethoxyphenyl)ethyl]-amino]-3-[3-[thieno[2,3-d]isoxazol-3-yl]phenoxy]-2-propanol hydrochloride | −36 | 50 |
| 1-[[(1-Methyl-3-phenyl)propyl]-amino]-3-[2-[1-methyl-1H—thieno-[3,2-c]pyrazol-3-yl]phenoxy]-2-propanol oxalate | −72 | 30 |
| 1-[[(1-methyl-2-phenoxy)ethyl]-amino]-3-[2-[1-methyl-1H—thieno- | −51 | 50 |

TABLE II-continued

ANTIHYPERTENSIVE ACTIVITY

| Compound | SHR mmHg | Dose mg/kg, PO |
|---|---|---|
| [3,2-c]pyrazol-3-yl]phenoxy]-2-propanol | | |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; and excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compound of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterials agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral multiple dose vials made of glass or plastic.

Examples of the compounds of this invention include:

1-[(1-methylethyl)amino]-3-[2-(thieno[2,3-d]isoxazol-3-yl)phenoxy]-2-propanol;

1-[(1-methylethyl)amino]-3-[3-(thieno[2,3-d]isoxazol-3-yl)phenoxy]-2-propanol;

1-[(1-methylethyl)amino]-3-[4-(thieno[2,3-d]isoxazol-3-yl)phenoxy]-2-propanol;

1-[(1,1s-dimethylethyl)amino-3-[2-(thieno[2,3-d]isoxazol-3-yl)phenoxy]-2-propanol;

1-[(1,1-dimethylethyl)amino]-3-[3-(thieno[2,3-d]isoxazol-3-yl)phenoxy]-2-propanol;

1-[(1,1-dimethylethyl)amino]-3-[4-(thieno[2,3-d]isoxazol-3-yl)phenoxy]-2-propanol;

1-[[(1-methyl-3-phenyl)propyl]amino]-3-[2-(thieno[2,3-d]isoxazol-3-yl)phenoxy]-2-propanol;

1-[[(1-methyl-3-phenyl)propyl]amino]-3-[3-(thieno[2,3-d]isoxazol-3-yl)phenoxy]-2-propanol;

1-[[(1-methyl-3-phenyl)propyl]amino]-3-[4-(thieno[2,3-d]isoxazol-3-yl)phenoxy]-2-propanol;

1-[[2-(3,4-dimethoxyphenyl)ethyl]amino]-3-[2-(thieno[2,3-d]isoxazol-3-yl)phenoxy]-2-propanol;

1-[[2-(3,4-dimethoxyphenyl)ethyl]amino]-3-[3-(thieno[2,3-d]isoxazol-3-yl)phenoxy]-2-propanol;

1-[[2-(3,4-dimethoxyphenyl)ethyl]amino]-3-[4-(thieno[2,3-]isoxazol-3-yl)phenoxy]-2-propanol;

1-[[(1,4-benzodioxan-2-yl)methyl]amino]-3-[2-(thieno[2,3-d]isoxazol-3-yl)phenoxy]-2-propanol;

1-[[(1,4-benzodioxan-2-yl)methyl]amino]-3-[3-(thieno[2,3-d]isoxazol-3-yl)phenoxy]-2-propanol;

1-[[(1,4-benzodioxan-2-yl)methyl]amino]-3-[4-(thieno[2,3-d]isoxazol-3-yl)phenoxy]-2-propanol;

1-[[2-(indol-3-yl)ethyl]amino]-3-[2-(thieno[2,3-d]isoxazol-3-yl)phenoxy]-2-propanol;

1-[[2-(indol-3-yl)ethyl]amino]-3-[3-(thieno[2,3-d]isoxazol-3-yl)phenoxy]-2-propanol;

1-[[2-(indol-3-yl)ethyl]amino]-3-[4-(thieno[2,3-d]isoxazol-3-yl)-phenoxy]-2-propanol;

3-[2-(thieno[2,3-d]isoxazol-3-yl)phenoxy]-1-[4-[2-(3,4,5-trimethoxyphenyl)ethyl]piperazin-1-yl]-2-propanol;

3-[3-(thieno[2,3-d]isoxazol-3-yl)phenoxy]-1-[4-[2-(3,4,5-trimethoxyphenyl)ethyl]piperazin-1-yl]-2-propanol;

3-[4-(thieno[2,3-d]isoxazol-3-yl)phenoxy]-1-[4-[2-(3,4,5-trimethoxyphenyl)ethyl]piperazin-1-yl]-2-propanol;

1-[(1-methylethyl)amino]-3-[2-[1-methyl-1H-thieno[3,2-c]pyrazol-3-yl]phenoxy]-2-propanol;

1-[(1-methylethyl)amino]-3-[3-[1-methyl-1H-thieno[3,2-c]pyrazol-3-yl]phenoxy]-2-propanol;

1-[(1-methylethyl)amino]-3-[4-[1-methyl-1H-thieno[3,2-c]pyrazol-3-yl]phenoxy]-2-propanol;

1-[(1,1-dimethylethyl)amino]-3-[2-[1-methyl-1H-thieno[3,2-c]pyrazol-3-yl]phenoxy]-2-propanol;

1-[(1,1-dimethylethyl)amino]-3-[3-[1-methyl-1H-thieno[3,2-c]pyrazol-3-yl]phenoxy]-2-propanol;
1-[(1,1-dimethylethyl)amino]-3-[4-[1-methyl-1H-thieno[3,2-c]pyrazol-3-yl]phenoxy]-2-propanol;
1-[[(1-methyl-3-phenyl)propyl]amino]-3-[2-[1-methyl-1H-thieno[3,2-c]pyrazol-3-yl]phenoxy]-2-propanol;
1-[[(1-methyl-3-phenyl)propyl]amino]-3-[3-[1-methyl-1H-thieno[3,2-c]pyrazol-3-yl]phenoxy]-2-propanol;
1-[[(1-methyl-3-phenyl)propyl]amino]-3-[4-[1-methyl-1H-thieno[3,2-c]pyrazol-3-yl]phenoxy]-2-propanol;
1-[[2-(3,4-dimethoxyphenyl)ethyl]amino]-3-[2-[1-methyl-1H-thieno[3,2-c]pyrazol-3-yl]phenoxy]-2-propanol;
1-[[2-(3,4-dimethoxyphenyl)ethyl]amino]-3-[3-[1-methyl-1H-thieno[3,2-c]pyrazol-3-yl]phenoxy]-2-propanol;
1-[[2-(3,4-dimethoxyphenyl)ethyl]amino]-3-[4-[1-methyl-1H-thieno[3,2-c]pyrazol-3-yl]phenoxy]-2-propanol;
1-[[(1,4-benzodioxan-2-yl)methyl]amino]-3-[2-[1-methyl-1H-thieno[3,2-c]pyrazol-3-yl]phenoxy]-2-propanol;
1-[[(1,4-benzodioxan-2-yl)methyl]amino]-3-[3-[1-methyl-1H-thieno[3,2-c]pyrazol-3-yl]phenoxy]-2-propanol;
1-[[(1,4-benzodioxan-2-yl)methyl]amino]-3-[4-[1-methyl-1H-thieno[3,2-c]pyrazol-3-yl]phenoxy]-2-propanol;
1-[[2-(indol-3-yl)ethyl]amino]-3-[2-[1-methyl-1H-thieno[3,2-c]pyrazol-3-yl]phenoxy]-2-propanol;
1-[[2-(indol-3-yl)ethyl]amino]-3-[3-[1-methyl-1H-thieno[3,2c]pyrazol-3-yl]phenoxy]-2-propanol;
1-[[2-(indol-3-yl)ethyl]amino]-3-[4-[1-methyl-1H-thieno[3,2-c]pyrazol-3-yl]phenoxy]-2-propanol;
3-[2-1-methyl-1H-thieno[3,2-c]pryazol-3-yl]phenoxy]-1-[4-[2-(3,4,5-trimethoxyphenyl)ethyl]piperazin-1-yl]-2-propanol;
3-[3-[1-methyl-1H-thieno[3,2-c]pyrazol-3-yl]phenoxy]-1-[4-[2-(3,4,5-trimethyoxyphenyl)ethyl]piperazin-1-yl]-2-propanol;
3-[4-[1-methyl-1H-thieno[3,2-c]pyrazol-3-yl]phenoxy]-1-[4-[2-(3,4,5-trimethoxyphenyl)ethyl]piperazin-1-yl]-2-propanol;
1-[(1-methylethyl)amino]-3-[2-[1H-thieno[3,2-c]pyrazol-3-yl]phenoxy]-2-propanol;
1-[(1-methylethyl)amino]-3-[3-[1H-thieno[3,2-c]pyrazol-3-yl]phenoxy]-2-propanol;
1-[(1-methylethyl)amino]-3-[4-[1H-thieno[3,2-c]pyrazol-3-yl]phenoxy]-2-propanol;
1-[(1,1-dimethylethyl)amino]-3-[2-[1H-thieno[3,2-c]pyrazol-3-yl]phenoxy]-2-propanol;
1-[(1,1-dimethylethyl)amino]-3-[3-[1H-thieno[3,2-c]pyrazole-3-yl]phenoxy]-2-propanol;
1-[(1,1-dimethylethyl)amino]-3-[4-[1H-thieno[3,2-c]pyrazol-3-yl]phenoxy]-2-propanol;
1-[[(1-methyl-3-phenyl)propyl]amino]-3-[2-[1H-thieno[3,2-c]pyrazol-3-yl]phenoxy]-2-propanol;
1-[[(1-methyl-3-phenyl)propyl]amino]-3-[3-[1H-thieno[3,2-c]pyrazol-3-yl]phenoxy]-2-propanol;
1-[[(1-methyl-3-phenyl)propyl]amino]-3-[4-[1H-thieno[3,2-c]pyrazol-3-yl]phenoxy]-2-propanol;
1-[[2-(3,4-dimethoxyphenyl)ethyl]amino]-3-[2-[1H-thieno[3,2-c]pyrazol-3-yl]phenoxy]-2-propanol;
1-[[2-(3,4-dimethoxyphenyl)ethyl]amino]-3-[3-[1h-thieno-[3,2-c]pyrazol-3-yl]phenoxy]-2-propanol;
1-[[2-(3,4-dimethoxypheny)ethyl]amino]-3-[4-[1H-thieno-[3,2-c]pyrazol-3-yl]phenoxy]-2-propanol;
1-[[(1,4-benzodioxan-2-yl)methyl]amino]-3-[2-[1H-thieno[3,2-c]pyrazol-3-yl]phenoxy]-2-propanol;
1-[[(1,4-benzodioxan-2-yl)methyl]amino]-3-[3-[1H-thieno[3,2-c]pyrazol-3-yl]phenoxy]-2-propanol;
1-[[(1,4-benzodioxan-2-yl)methyl]amino]-3-[4-[1h-thieno[3,2-c]pyrazol-3-yl]phenoxy]-2-propanol;
1-[[2-(indol-3-yl)ethyl]amino]-3-[2-[1H-thieno[3,2-c]pyrazol-3-yl]phenoxy]-2-propanol;
1-[[2-(indol-3-yl)ethyl]amino]-3-[3-[1H-thieno[3,2-c]pyrazol-3-yl]phenoxy]-2-propanol;
1-[[2-(indol-3-yl)ethyl]amino]-3-[4-[1H-thieno[3,2-c]pyrazol-3-yl]phenoxy]-2-propanol;
3-[2-[1H-thieno[3,2-c]pyrazol-3-yl]phenoxy]-1-[4-[2-(3,4,5-trimethoxyphenyl)ethyl]piperazin-1-yl]-2-propanol;
3-[3-[1H-thieno[3,2-c]pyrazol-3-yl]phenoxy]-1-[4-[2-(3,4,5-trimethoxyphenyl)ethyl]piperazin-1-yl]-2-propanol;
3-[4-[1H-theino[3,2-c]pyrazol-3-yl]phenoxy]-1-[4-[2-(3,4,5-trimethoxyphenyl)ethyl]piperazin-1-yl]-2-propanol;
3-(2-methoxyphenyl)thieno[2,3-d]isoxazole;
3-(3-methoxyphenyl)thieno[2,3-d]isoxazole;
3-(4-methoxyphenyl)thieno[2,3-d]isoxazole;
3-(2-hydroxyphenyl)thieno[2,3-d]isoxazole;
3-(3-hydroxyphenyl)thieno[2,3-d]isoxazole;
3-(4-hydroxyphenyl)thieno[2,3-d]isoxazole;
3-(2-epoxymethoxyphenyl)thieno[2,3-d]isoxazole;
3-(3-epoxymethoxyphenyl)thieno[2,3-d]isoxazole;
3-(4-epoxymethoxyphenyl)thieno[2,3-d]isoxazole;
1-methyl-3-(2-methoxyphenyl)-1H-thieno[3,2-c]pyrazole;
1-methyl-3-(3-methoxyphenyl)-1H-thieno[3,2-c]pyrazole;
1-methyl-3-(4-methoxyphenyl)-1H-thieno[3,2-c]pyrazole;
3-(2-hydroxyphenyl)-1-methyl-1H-thieno[3,2-c]pyrazole;
3-(3-hydroxyphenyl)-1-methyl-1H-thieno[3,2-c]pyrazole;
3-(4-hydroxyphenyl)-1-methyl-1H-thieno[3,2-c]pyrazole;
3-[2-epoxymethoxyphenyl]-1-methyl-1H-thieno[3,2-c]pyrazole;
3-[3-epoxymethoxyphenyl]-1-methyl-1H-thieno[3,2-c]pyrazole;
3-[4-epoxymethoxyphenyl]-1-methyl-1H-thieno[3,2-c]pyrazole;
3-(2-methoxyphenyl)-1H-thieno[3,2-c]pyrazole;
3-(3-methoxyphenyl)-1H-thieno[3,2-c]pyrazole;
3-(4-methoxyphenyl)-1H-thieno[3,2-c]pyrazole;
3-(2-hydroxyphenyl)-1H-thieno[3,2-c]pyrazole;
3-(3-hydroxyphenyl)-1thieno[3,2-c]pyrazole;
3-(4-hydroxyphenyl)-1H-thieno[3,2-c]pyrazole;
3-[2-epoxymethoxyphenyl]-1H-thieno[3,2-c]pyrazole;
3-[3-epoxymethoxyphenyl]-1H-thieno[3,2-c]pyrazole;
3-[4-epoxymethoxyphenyl]-1H-thieno[3,2-c]pyrazole;
(3-bromothien-2-yl) (2-methoxyphenyl)methanone;
(3-bromothien-2-yl) (3-methoxyphenyl)methanone;
(3-bromothien-2-yl) (4-methoxyphenyl)methanone;
(3-bromothien-2-yl) (2-methoxyphenyl)methanone oxime;
(3-bromothien-2-yl) (3-methoxyphenyl)methanone oxime;
(3-bromothien-2-yl) (4-methoxyphenyl)methanone oxime;
(3-bromothien-2-yl) (2-methoxyphenyl)methanone hydrazone;

(3-bromothien-2-yl) (3-methoxyphenyl)methanone hydrazone;
(3-bromothien-2-yl) (4-methoxyphenyl)methanone hydrazone;
1-[[2-(3,4-dimethoxyphenyl)ethyl]amino]-3-[2-[1H-thieno[3,2-c]pyrazol-3-yl]phenoxy]-2-propanol;
1-[[2-(3,4-dimethoxyphenyl)ethyl]amino]-3-[3-[1H-thieno[3,2-c]pyrazol-3-yl]phenoxy]-2-propanol;
1-[[2-(3,4-dimethoxyphenyl)ethyl]amino]-3-[4-[1H-thieno[3,2-c]pyrazol-3-yl]phenoxy]-2-propanol;
1-[[2-[(2-methoxy)phenoxy]ethyl]amino]-3-[2-[1-methyl-1H-thieno[3,2-c]pyrazol-3-yl]phenoxy]-2-propanol;
1-[[2-[(2-methoxy)phenoxy]ethyl]amino]-3-[3-[1-methyl-1H-thieno[3,2-c]pyrazol-3-yl]phenoxy]-2-propanol;
1-[[2-[(2-methoxy)phenoxy]ethyl]amino]-3-[4-[1-methyl-1H-thieno[3,2-c]pyrazol-3-yl]phenoxy]-2-propanol;
1-[[(1-Methyl-2-phenoxy)ethyl]amino]-3-[2-[1H-thieno[3,2-c]pyrazol-3-yl]phenoxy]-2-propanol;
1-[[(1-Methyl-2-phenoxy)ethyl]amino]-3-[3-[1H-thieno[3,2-c]pyrazol-3-yl]phenoxy]-2-propanol;
1-[[(1-Methyl-2-phenoxy)ethyl]amino]-3-[4-[1H-thieno[3,2-c]pyrazol-3-yl]phenoxy]-2-propanol;
1-[[[2-[(2-methoxy)phenoxy]-1-methyl]ethyl]amino]-3-[2-[1-methyl-1H-thieno[3,2-c]pyrazol-3-yl]phenoxy]-2-propanol;
1-[[[2-[(2-methoxy)phenoxy]-1-methyl]ethyl]amino]-3-[3-[1-methyl-1H-thieno[3,2-c]pyrazol-3-yl]phenoxy]-2-propanol; and
1-[[[2-[(2-methoxy)phenoxy]-1-methyl]ethyl]amino]-3-[4-[1-methyl-1H-thieno[3,2-c]pyrazol-3-yl]phenoxy]-2-propanol.

The following examples are given for illustrative purposes and are not to be considered as limiting the invention disclosed herein. All temperatures are given in degrees Celsius.

EXAMPLE 1

(3-Bromothien-2-yl) (2-methoxyphenyl)methanone

A solution of 3-bromo-2-lithiothiophene was prepared by adding a stock solution of phenyllithium (27.5 ml, 2.0M) to a stirred solution of 3-bromothiophene (8.5 g) in 50 ml of anhydrous ether. Stirring was continued at room temperature under nitrogen for 16 hours.

In a 500 ml three-necked flask was placed 14 g of o-methoxybenzoyl chloride in 50 ml of tetrahydrofuran. The solution was cooled to −60° before the above-mentioned lithio derivative was added dropwise. The mixture was stirred at −60° for 30 minutes, allowed to warm to room temperature by removing the cooling bath and allowed to stand at ambient temperature for four hours.

Quenching with water (500 ml) gave an oily precipitate which was taken up in ether. The combined etheral solution was washed, dried and concentrated to give a thick oil which was chromatographed over alumina packed in hexane. Elution with hexane removed most of the unreacted starting materials and further elution with 50% ether/hexane gave 6.2 g of an oil. Trituration of the crude product, with cooling and scratching, afforded 5.20 g of a solid, m.p. 103°–104° C.

ANALYSIS: Calculated for $C_{12}H_9BrO_2S$: 48.49%C, 3.05%H. Found: 48.39%C, 3.21%H.

EXAMPLE 2

(3-bromothien-2-yl) (2-methoxyphenyl)methanone oxime

A solution of 20 g of (3-bromothien-2-yl) (2-methoxyphenyl)methanone in 200 g of pyridine containing 10 g of hydroxylamine hydrochloride was heated at 100° for 10 minutes and thereafter allowed to cool. After standing at room temperature for 16 hours, the solution was poured onto 600 g of ice water and the organics were extracted into ether. The combined ether solution was washed with 1N hydrochloric acid and water, and dried over anhydrous magnesium sulfate. Evaporation of the solvent under vacuum left a solid residue which was recrystallized from ether/hexane to give prisms, m.p. 129°–130° C.

ANALYSIS: Calculated for $C_{12}H_{10}BrNO_2S$: 46.16%C, 3.23%H, 4.49%N. Found: 46.25%C, 3.35%H, 4.59%N.

EXAMPLE 3

3-(2-Methoxyphenyl)thieno[2,3-d]isoxazole

A solution of 12.0 g of (3-bromothien-2-yl) (2-methoxyphenyl)methanone oxime in 220 ml of ethoxyethanol was combined with 15 ml of water containing 4.3 g of potassium hydroxide pellets (85%) and the mixture was stirred at 110° for 10 minutes and thereafter 0.28 g of cuprous chloride was added. Stirring was maintained at this temperature under nitrogen for one hour.

The mixture was cooled, quenched with water and extracted three times with chloroform with filtration, and the layers were separated. The combined chloroform solution was washed with water, dried, and concentrated in vacuo to a thick oil. Purification of the crude product was effected by column chromatography over alumina packed in ether. Elution with a large excess of ether afforded 6.2 g of the desired isoxazole of analytical purity, m.p. 47°–49° C.

ANALYSIS: Calculated for $C_{12}H_9NO_2S$: 62.32%C, 3.92%H, 6.06%N. Found: 62.13%C, 4.21%H, 6.03%N.

EXAMPLE 4

3-(2-Hydroxyphenyl)thieno[2,3-d]isoxazole

To a solution of 23 g of 3-(2-methoxyphenyl)-thieno[2,3-d]isoxazole in 450 ml of dichloromethane was added a boron tribromide solution in dichloromethane (150 ml, 1M solution) over one hour. The reaction mixture was stirred for an additional one hour at room temperature and then poured over 600 ml of ice water. A precipitate was filtered off and washed with 50% ether/ethyl acetate. The aqueous phase was also extracted with 50% ether/ethyl acetate and the combined solvent solution was washed with water and dried over anhydrous magnesium sulfate. Evaporation of the solvent solution left 17 g of a solid which was passed through a silica gel column packed in hexane and eluted with 50% ether/hexane. The resultant solid was recrystallized from ether/hexane to give 15 g of a solid, m.p. 121°–123° C.

ANALYSIS: Calculated for $C_{11}H_7NO_2S$: 60.81%C, 3.25%H, 6.45%N. Found: 61.07%C, 3.34%H, 6.47%N.

EXAMPLE 5

3-(2-Epoxymethoxyphenyl)thieno[2,3-d]isoxazole

A mixture of 6.3 g of 3-(2-hydroxyphenyl)thieno[2,3-d]isoxazole, 5 g of epibromohydrin and 2.6 g of potassium carbonate in 37 ml of acetonitrile was stirred under nitrogen at 70°–80° C. until completion of the reaction. The reaction was complete after 28 hours and the mixture was left to cool to room temperature. Quenching with water, extraction with ether/ethyl acetate (1:1), washing and drying (over anhydrous magnesium sulfate) gave 6.34 g of a crude oil. The epoxide was separated by high performance liquid chromatography (HPLC hereafter) using ethyl acetate/hexane (2:1) as an eluent, yielding 5.22 g of crystal. This was recrystallized from ether/hexane, m.p. 65°–67° C.

ANALYSIS: Calculated for $C_{14}H_{11}NO_3S$: 61.53%C, 4.06%H, 5.12%N. Found: 61.59%C, 4.13%H, 5.21%N.

EXAMPLE 6

1-[(1-Methylethyl)amino]-3-[2-(thieno[2,3-d]isoxazol-3-yl)phenoxyl-2-propanol maleate To a stirred solution of 2.9 g of epibromohydrin in 15 ml of dimethylformamide (DMF hereafter) were added 4.0 g of 3-(2-hydroxyphenyl)thieno[2,3-d]isoxazole and 4 g of potassium carbonate. After three hours of heating at 50°–60° C. under nitrogen, the reaction mixture was poured into 200 ml of water and the organics were extracted into ether. Concentration of the ether solution after washing and drying (over anhydrous magnesium sulfate) left 5 g of a crude solid. This solid was passed through a silica gel column packed in hexane and eluted with 50% ether/hexane and then with ether to give 4.3 g of a solid.

To 2.3 g of this solid was added 15 ml of ethanol and 10 ml of isopropylamine. This solution was stirred at reflux for 30 minutes under nitrogen. Evaporation of the excess isopropylamine and ethanol left a residue which was taken up in 200 ml of ether. The ether solution was shaken with 10% aqueous hydrochloric acid solution and discarded. The acidic aqueous solution was basified with 10% sodium hydroxide solution and then extracted three times with ether. Evaporation of this ether solution after washing and drying (over anhydrous magnesium sulfate) left 2.75 g of an oil. This oil was converted to the maleate salt by mixing the oil in ether and adding an excess of ethereal maleic acid. The precipitate was recrystallized from methanol/acetone/ether to give 2.7 g of a crystalline solid, m.p. 86°–89° C.

ANALYSIS: Calculated for $C_{17}H_{20}N_2O_3S \cdot C_4H_4O_4$: 56.24%C, 5.39%H, 6.25%N. Found: 56.03%C, 5.44%H, 6.22%N.

EXAMPLE 7

1-[(1,1-Dimethylethyl)amino]-3-[2-(thieno[2,3-d]isoxazol-3-yl)phenoxy]-2-propanol maleate A mixture of 2.8 g of 3-(2-hydroxyphenyl)thieno[2,3-d]isoxazole, 2.1 g of epibromohydrin, 3 g of anhydrous potassium carbonate in 6 ml of dimethylformamide was stirred at 90° for 6 hours. The cooled mixture was quenched with water, and the organics were extracted into ether, washed and dried over magnesium sulfate. Evaporation of the solvent left a crude oil which was passed through a column of silica gel packed in hexane. Elution with ether/hexane (1:1) afforded 2.2 g of an epoxide essentially free from impurities.

The epoxide was then gently refluxed with 10 ml of ethanol and 7 ml of t-butylamine for 3 hours. The excess solvent and amine were removed in vacuo, leaving an oily residue which was dissolved in 300 ml of ether (suspensions were removed by filtration at this point). The basic material was extracted into a dilute solution of hydrochloric acid (10%) and basification of the acidic solution with 20% sodium hydroxide solution yielded the desired amino alcohol of high purity. The oily amine thus obtained was taken up in ether, washed four times with water and dried. Treatment of this solution with a large excess of ethereal maleic acid gave 2.8 g of a crystallize salt which was purified by recrystallization from methanol/ether, m.p. 128°–130° C.

ANALYSIS: Calculated for $C_{18}H_{22}N_2O_3S \cdot C_4H_4O_4$: 57.13%C, 5.66%H, 6.06%N. Found: 56.75%C, 5.77%H, 5.94%N.

EXAMPLE 8

1-[[(1-Methyl-3-phenyl)propyl]amino]-3-[2-(thieno[2,3-d]isoxazol-3-yl)phenoxy]-2-propanol A mixture of 3.5 g of 3-(2-epoxymethoxyphenyl)thieno[2,3-d]isoxazole and 1.5 g (16.7 mmoles) of 2-amino-4-phenylbutane in 7 ml of ethyl acetate was refluxed until completion of the reaction (24 hours). The cooled solution was diluted with a 1:1 solution of ether/ethyl acetate and extracted with 2N hydrochloric acid (ice-cold) until the pH became 2. The aqueous solution was basified with concentrated ammonium hydroxide, whereupon a precipitate formed (stirring was necessary). The oily product was extracted into a 1:1 ether/ethyl acetate solution, washed with water and dried over anhydrous magnesium sulfate. The solution was concentrated to give a crude oil which was run through an HPLC to obtain 2.11 g of an oil.

ANALYSIS: Calculated for $C_{24}H_{26}N_2O_3S$: 68.22%C, 6.20%H, 6.63%N. Found: 68.31%C, 6.38%H, 6.51%N.

EXAMPLE 9

1-[[2-(3,4-Dimethoxyphenyl)ethyl]amino]-3-[2-(thieno[2,3-d]isoxazol-3-yl)phenoxy]-2-propanol A mixture prepared from 3.5 g of 3-(2-epoxymethoxyphenyl)thieno[2,3-d]isoxazole, 2.9 g of beta-(3,4-dimethoxyphenyl)ethylamine and 15 ml of ethyl acetate was stirred at reflux for 18 hours under nitrogen. The reaction mixture was then diluted with 200 ml of ether and 35 ml of ethyl acetate. This organic solution was shaken with 200 ml of 10% hydrochloric acid solution and discarded. The acidic aqueous phase was basified with 10% sodium hydroxide solution and extracted with a 6:3:1 solution of ether/ethyl acetate/dichloromethane. Evaporation of this organic solution after washing and drying (over anhydrous magnesium sulfate) left 8 g of an oil. This oil was purified by HPLC with 30% methanol/dichloromethane used as an eluent. Similar fractions were combined and evaporated to give 4 g of an oil. Trituration with 5 ml of ether gave a solid which was recrystallized twice from isopropyl ether/acetone/ether to give 2.3 g of crystals, m.p. 66°–68° C.

ANALYSIS: Calculated for $C_{24}H_{26}N_2O_5S$: 63.42%C, 5.77%H, 6.16%N. Found: 63.13%C, 5.86%H, 6.02%N.

EXAMPLE 10

1-[[(1,4-Benzodioxan-2-yl)methyl]amino]-3-[2-(thieno[2,3-d]isoxazol-3-yl)phenoxy]-2-propanol hydrochloride A mixture of 3-(2-hydroxyphenyl)thieno[2,3-d]isoxazole (2 g), epibromohydrin (1.44 g), potassium carbonate (2 g) and 10 ml of dimethylformamide was stirred under nitrogen at 50°-60° C. for three hours. The reaction mixture was then cooled, poured into 200 ml of water and extracted twice with ether and once with ethyl acetate. Concentration of the ether/ethyl acetate solution after washing and drying (over anhydrous magnesium sulfate) left 3.5 g of an oil which was column chromatographed twice (silica gel packed in hexane). Elution of the first column with 50% ether/hexane and the second with dichloromethane (DCM hereafter) gave 2.1 g of a solid.

This material was refluxed in 15 ml of ethanol with 1.33 g of 2-aminomethyl-1,4-benzodioxane (see, for instance, Green et al, J. Med. Chem. 12, 326 (1969)) for 2.5 hours under nitrogen. Concentration of this reaction mixture left a residue which was taken up in 20:80 ethyl acetate/ether. The organic solution was shaken with 10% hydrochloric acid solution and discarded. The acidic aqueous layer was basified with 10% sodium hydroxide solution and thereafter extracted three times with 90:10 ether/ethyl acetate. Concentration of the organic solution after washing and drying (over anhydrous magnesium sulfate) left 2.47 g of an oil. This oil was combined 1.27 g of a batch prepared earlier in a similar manner. The combined batch was purified by preparative HPLC and eluted with 3% methanol/dichloromethane. Evaporation of similar fractions gave 2.2 g of an oil which was converted to the hydrochloride salt by mixing the oil with ether and adding an excess of ethereal hydrochloric acid. Recrystallization of the salt from methanol/acetone/ether gave 1.6 g of a solid, m.p. 128°-130° C.

ANALYSIS: Calculated for $C_{23}H_{22}N_2O_5S \cdot HCl$: 58.16%C, 4.67%H, 5.89%N. Found: 58.41%C, 4.87%H, 6.33%N.

EXAMPLE 11

1-[[2-(Indol-3-yl)ethyl]amino]-3-[2-(thieno[2,3-d]isoxazol-3-yl)phenoxy]-2-propanol hydrochloride A mixture of 3.6 g of 3-(2-epoxymethoxyphenyl)thieno[2,3-d]isoxazole, 2.8 g of tryptamine and 15 ml of ethyl acetate was stirred at reflux for 16 hours. The cooled mixture was diluted with 150 ml of ethyl acetate and 150 ml of ether and extracted with 10% hydrochloric acid (ice-cold) until the pH became 2. The oily precipitate which separated gradually solidified. The crystals were then filtered, washed with water and digested with concentrated $NH_3$.

The fluffy product (free base) and extracted into 300 ml of ethyl acetate/ether (1:1), washed with water and dried over anhydrous magnesium sulfate.

Removal of solvents under reduced pressure left a viscous oil which was redissolved in ether containing 20% of acetone. Treatment of this solution with a large excess of ethereal hydrochloric acid afforded a solid, m.p. 170°-172° C. Recrystallization of the product from methanol/ethyl acetate gave 1.99 g of crystals, m.p. 171°-172.5° C.

ANALYSIS: Calculated for $C_{24}H_{23}N_3O_3S \cdot HCl$: 61.46%C, 4.94%H, 8.96%N. Found: 61.71%C, 5.36%H, 8.97%N.

EXAMPLE 12

3-(2-Methoxyphenyl)-1-methyl-1H-thieno[3,2-c]pyrazole

A mixture of (3-bromothien-2-yl)(2-methoxyphenyl)methanone (10 g), methyl hydrazine (10 ml) and ethylene glycol (70 ml) was stirred at 110°-120° C. for two hours under nitrogen. The reaction mixture was then allowed to cool to room temperature, quenched with 125 ml of water and the organics were extracted into a 50:50 ether/ethyl acetate solution. Washing, drying (over anhydrous magnesium sulfate) and then evaporation of the solvents left 10 g of an oil. This oil was passed through a silica gel column packed in hexane and eluted with dichloromethane to give 7 g of an oil which subsequently crystallized. Recrystallization from ether/hexane gave 4 g of a crystalline solid, m.p. 94°-97° C.

ANALYSIS: Calculated for $C_{13}H_{12}N_2OS$: 63.90%C, 4.95%H, 11.47%N. Found: 63.83%C, 4.99%H, 11.62%N.

EXAMPLE 13

3-(2-Hydroxyphenyl)-1-methyl-1H-thieno[3,2-c]pyrazole

To a solution of 3-(2-methoxyphenyl)-1-methyl-1H-thieno[3,2-c]pyrazole (4.2 g) in 30 ml of dichloromethane was added dropwise 24 ml of a stock solution of $BBr_3$ in dichloromethane. The mixture warmed up spontaneously and a precipitate begain to deposit. After stirring at ambient temperature for 2 hours, the reaction mixture was quenched with 50 ml of 1H hydrochloric acid. Stirring was continued overnight whereupon the mixture became almost clear. The organic layer was diluted with ether, the phases were separated, and the aqueous layer was basified with concentrated $NH_3$ and extracted three times with 200 ml total of ether. The combined organic solution was washed with water, dried (over anhydrous magnesium sulfate) and concentrated to a solid. Purification of the crude product was effected by passing it through a column of silica gel packed in dichloromethane, which afforded 3.48 g of crystals. They were further purified by recrystallization from ether/hexane, m.p. 112°-113° C.

ANALYSIS: Calculated for $C_{12}H_{10}N_2OS$: 65.58%C, 4.38%H, 12.17%N. Found: 62.73%C, 4.39%H, 12.17%N.

EXAMPLE 14

3-[2-Epoxymethoxyphenyl)-1-methyl-1H-thieno[3,2-c]pyrazole

A mixture of 14 g of 3-(2-hydroxyphenyl)-1-methyl-1H-thieno[3,2-c]pyrazole, 10 g of epibromohydrin, 5 g of potassium carbonate and 75 ml of acetonitrile was stirred under nitrogen at 70°-80° C. After 16 hours of stirring, thin layer chromatography (1:1 hexane/ethyl acetate) showed residual starting material. Therefore, 2 g of epibromohydrin and 10 ml of dimethylformamide were added and the mixture was stirred overnight at 92° C., and thereafter quenched, extracted with ether/ethyl acetate (1:1), washed and dried (over anhydrous magnesium sulfate). The epoxide was separated from other by-products using HPLC (eluent=DCM).

ANALYSIS: Calculated for $C_{15}H_{19}N_2O_2S$: 62.19%C, 4.93%N, 9.78%N. Found: 62.98%C, 4.98%H, 9.74%N.

EXAMPLE 15

1-[1-Methylethylamino]-3-[2-[1-methyl-1H-thieno[3,2-c]pyrazol-3-yl]phenoxy]-2-propanol dihydrochloride A mixture of 3.3 g of 3-(2-hydroxyphenyl)-1-methyl-1H-thieno[3,2-c]pyrazole, 2.74 g of epibromohydrin, 3.2 g of anhydrous potassium carbonate and 12 ml of dimethylformamide was stirred at 60°–70° for 16 hours. The cooled mixture was diluted with 300 ml of ethyl acetate/ether (50:50) and 100 ml of water. The organic solution was separated, and the aqueous layer was extracted twice with ethyl acetate/ether (50:50). The combined organic extract was washed with water, dried and concentrated to given an oil.

The crude epoxide was fed to a silica gel column packed in hexane. Elution with dichloromethane yielded, as a main fraction, 3.5 g of the desired epoxide of 95% purity.

The epoxide so obtained was refluxed with 5 ml of isopropylamine and 10 ml of ethanol for 16 hours. The excess reagent and solvent were removed in vacuo leaving an oily residue. The crude product was taken up in ethyl acetate/ether (1:3), washed and dried. Treatment of the filtered solution with ethereal hydrochloric acid gave a gummy precipitate which crystallized upon trituration with methanol, m.p. 179°–182° C. Recrystallization from methanol/acetone afforded 3.6 g of crystals without change in the melting range.

ANALYSIS: Calculated for $C_{18}H_{23}N_3O_2S.HCl$: 51.67%C, 6.07%H, 10.04%N. Found: 51.78%C, 6.08%H, 9.98%N.

EXAMPLE 16

1-[(1,1-Dimethylethyl)amino]-3-[2-[1-methyl-1H-thieno[3,2-c]pyrazol-3-yl]phenoxy]-2-propanol dihydrochloride A mixture of 3 g of 3-[2-epoxymethoxyphenyl]-1-methyl-1H-thieno[3,2-c]pyrazole, 1.27 ml of tertiary butylamine (large excess) and 10 ml of ethanol was refluxed until completion of the reaction (5 hours). The reaction mixture was cooled to room temperature and quenched with water. The product was taken up with 1:1 ether/ethyl acetate, washed and dried. Evaporation of the solvents afforded a crude oil which was extracted with 2N hydrochloric acid (ice-cold). Basification of the acidic solution with 20% sodium hydroxide solution yielded the desired amine in high purity. The oily compound was taken up in ether, washed with water and dried over anhydrous magnesium sulfate. Treatment of this solution with ethereal hydrochloric acid gave 2.5 g of a crystalline salt which was purified by recrystallization from acetone/ethanol (m.p. 133°–135° C.).

ANALYSIS: Calculated for $C_{19}H_{25}N_3O_2S.2HCl$: 52.77%C, 6.29%H, 9.72%N. Found: 52.68%C, 6.25%H, 9.57%N.

EXAMPLE 17

1-[[(1-Methyl-3-phenyl)propyl]amino]-3-[2-[1-methyl-1H-thieno[3,2-c]pyrazol-3-yl]phenoxy]-2-propanol oxalate A 2.2 g sample of 3-[2-epoxymethoxyphenyl]-1-methyl-1H-thieno[3,2-c]pyrazole was refluxed with 1.0 g of 2-amino-4-phenylbutane in 7 ml of ethyl acetate. The reaction was complete after 28 hours and the mixture was allowed to cool down to room temperature. The solution was then quenched with water and taken up in ethyl ether/ethyl acetate (1:1). Extraction with 2N hydrocholric acid (cold) and basification with ammonium hydroxide left an oil which was extracted into ethyl acetate/ethyl ether (1:1), washed with water and dried over anhydrous magnesium sulfate. Evaporation of the solvents left 1.92 g of an oil. The amine was purified by HPLC using 1:1 methanol/ethyl acetate as an eluent. The oily product was converted to the oxalate salt by dissolving it in ether and adding a saturated solution of ethereal oxalic acid. This afforded a fluffy solid. Recrystallization of the product from ethyl acetate gave a solid having a melting point of 157°–160° C.

ANALYSIS: Calculated for $C_{27}H_{31}O_6N_3S$: 61.70%C, 5.94%H, 7.99%N. Found: 61.76%C, 6.07%H, 7.93%N.

EXAMPLE 18

3-[2-[1-Methyl-1H-thieno[3,2-c]pyrazol-3-yl]phenoxy]-1-[3,4,5-trimethoxyphenyl)piperazin-4-yl]-2-propanol dimaleate A mixture of 2 g of 3-[2-epoxymethoxyphenyl]-1-methyl-1H-thieno[3,2-c]pyrazole and 2.4 g of 1-[2-(3,4,5,-trimethoxyphenyl)ethyl]piperazine was refluxed in 15 ml of ethyl acetate for 24 hours. The reaction mixture was cooled to room temperature and quenched with ice-water. The organics were extracted into ether/ethyl acetate (1:1) and washed thoroughly with water. Drying over anhydrous magnesium sulfate and evaporation of solvents resulted in 2.2 g of a crude thick oil. This was converted to the maleate salt by dissolving it into a small amount of ether and adding thereto a saturated ethereal maleic acid solution. A fluffy salt precipitated out immediately, which was recrystallized from methanol/ether to give 1.6 g of a solid.

ANALYSIS: Calculated for $C_{30}H_{38}N_4O_5S.2C_4H_4O_4$: 56.62%C, 5.65%H, 7.13%N. Found: 56.61%C, 5.80%H, 6.94%N.

EXAMPLE 19

(3-Bromothien-2-yl) (2-methoxyphenyl)methanone hydrazone

A mixture prepared from 10 g of (3-bromothien-2-yl) (2-methoxyphenyl)methanone, 10 ml of hydrazine hydrate and 75 ml of ethylene glycol was stirred at 130°–135° C. for six hours under nitrogen. The reaction mixture was then allowed to cool to room temperature and quenched with water and the organics were extracted into ether. Washing, drying (over anhydrous magnesium sulfate) and then evaporation of the ether left 10 g of a crude solid. This material was passed through a silica gel column packed in hexane and eluted with 15% and then 50% ether/hexane to give 3 g of crystals and 5 g of an oil. The product was recrystallized from a mixture of 1:1:1 ether/ethyl acetate/hexane, m.p. 120°–122° C.

ANALYSIS: Calculated for $C_{12}H_{11}BrN_2OS$: 46.31%C, 3.56%H, 9.00%N. Found: 46.21%C, 3.60%H, 9.01%N.

EXAMPLE 20

3-(2-Methoxyphenyl)-1H-thieno[3,2-c]pyrazole

A mixture of 5.23 g of (3-bromthien-2-yl) (2-methoxyphenyl)methanone hydrazone and 47 ml of ethoxyethanol was heated at 75° C. and to it a solution of potassium hydroxide in water (1.88 g in 9.15 ml) was added. The reaction mixture was blanketed with nitrogen. After stirring for 10 minutes, 50 mg of CuCl was then added and stirring was continued until completion of the reaction (45 minutes). The reaction mixture was then allowed to cool to room temperature, quenched with water and the organics were extracted into ether/ethyl acetate (1:1). Washing, drying (over anhydrous magnesium sulfate) and then evaporation of the ether/ethyl acetate solution gave an oil containing some crystals. The oil was passed through a silica gel column packed in dichloromethane to give 2.07 g of crystals. This material was combined with another material prepared in the same manner. The combined product (3.1 g) was recrystallized from ether/hexane.

ANALYSIS: Calculated for $C_{12}H_{10}N_2OS$: 62.59%C, 4.38%H, 12.16%N. Found: 62.26%C, 4.47%H, 12.33%N.

EXAMPLE 21

(3-Bromothien-2-yl) (3-methoxyphenyl)methanone

A solution of phenyllithium (210 ml, 2.1M in cyclohexane) was added dropwise to a solution of 66 g of 3-bromothiophene in 400 ml of anhydrous ether at 5° C. The entire process was conducted under nitrogen. After the addition, the solution was stirred overnight under nitrogen. The resultant solution was then added dropwise to a solution of m-methoxybenzoyl chloride (90 g) in 600 ml of tetrahydrofuran at −70° C. over two hours and thereafter stirring was continued for two hours at the same temperature. The reaction was then quenched with water, the organics were extracted into ether, and the ether phase was washed with 10% sodium hydroxide solution and water, and dried over anhydrous magnesium sulfate. Upon evaporation of the solvent, an oily liquid was obtained which was chromatographed over alumina. Elution with hexane and thereafter with 10%, 20% and 50% ether/hexane gave 89.1 g of an oil which was vacuum distilled.

ANALYSIS: Calculated for $C_{12}H_9O_2BrS$: 48.49%C, 3.05%H. Found: 48.17%C, 3.12%H.

EXAMPLE 22

(3-Bromothien-2-yl) (3-methoxyphenyl)methanone oxime

A mixture prepared from 7 g of (3-bromothien-2-yl) (3-methoxyphenyl)methanone, 3.09 g of hydroxyamine hydrochloride and 40 ml of pyridine was stirred at room temperature overnight and thereafter heated at 100°-115° C. for 4 hours. The mixture was then quenched with water, the organics were extracted into ether, and the ether solution was washed with 3N hydrochloric acid and water and dried over anhydrous magnesium sulfate. Evaporation of the ether left a residue which crystallized upon standing overnight. The crude solid was passed through a column (alumina packed in hexane) with 15% ether/hexane used as an eluent. The solid was recrystallized from ether/hexane to give a crystalline product (6.4 g, m.p. 100°-103° C).

ANALYSIS: Calculated for $C_{12}H_{10}BrNO_2S$: 46.16%C, 3.22%H, 4.48%N. Found: 45.96%C, 3.26%H, 4.45%N.

EXAMPLE 23

3-(3-Methoxyphenyl)thieno[3,2-d]isoxazole

A mixture of 10.0 g of (3-bromothien-2-yl) (3-methoxyphenyl)methanone oxime, 3.6 g of potassium hydroxide (dissolved in 10 ml of water) and 100 ml of 2-ethoxyethanol was stirred under nitrogen at 105°-110° C. for 1 hour. Cuprous chloride (0.16 g) was added and the reaction mixture was heated for an additional 1 hour at 105°-110° C. Water was added to quench the reaction and the organics were extracted into ether. The ether phase was washed three times with water and dried over anhydrous magnesium sulfate.

Evaporation of the solvent left a residue which was purified by column chromatography over alumina packed in hexane. Elution with 15% ether/hexane gave a solid, which was recrystallized from ether/hexane to yield 5 g of product, m.p. 51°-52° C.

ANALYSIS: Calculated for $C_{13}H_9NO_2S$: 62.32%C, 3.92%H, 6.06%N. Found: 62.20%C, 3.82%H, 6.02%N.

EXAMPLE 24

3-(3-Hydroxyphenyl)thieno[2,3-d]isoxazole

Eight grams of 3-(3-methoxyphenyl)thieno[2,3-d]isoxazole was stirred with 80 g of pyridine hydrochloride for nine hours under nitrogen at 140° C. The reaction mixture was then allowed to cool and quenched with water. The organics were extracted into ether/ethyl acetate (1:1), which was then washed once with 3N hydrochloric acid and three times with water an dried over anhydrous magnesium sulfate. Evaporation of the solvents left 4 g of an oil, which was passed through a silica gel column packed in hexane. Elution of the column with 5% ethyl acetate/dichloromethane and recrystallization of the resultant solid from ether/hexane gave 3 g of a solid, m.p. 114°-116° C.

ANALYSIS: Calculated for $C_{11}H_7NO_2S$: 60.81%C, 3.25%H. Found: 60.59%C, 3.45%H.

EXAMPLE 25

1-[(1-Methylethyl)amino]-3-(thieno[2,3-d]isoxazole-3-yl)phenoxy]-2-propanol maleate To a stirred solution of 3.5 g of epibromohydrin in 10 ml of dimethylformamide was added 4.0 g of 3-(3-hydroxyphenyl)thieno[2,3-d]isoxazole and 4.0 g of potassium carbonate. After six hours of heating at 70°-80° C. under nitrogen the reaction mixture was quenched with 200 ml of water and the organics were extracted into ethyl acetate/ether (1:1). Concentration of the solution after washing and drying left 5.5 g of an oil. This oil was then stirred with ethanol (15 ml) and isopropylamine (5 ml) under nitrogen at reflux for three hours. Evaporation of the excess isopropylamine and ethanol yielded an oil which was taken up in 250 ml of ether. The ether solution was shaken with 10% hydrochloric acid and then the ether phase was discarded. The acidic solution was basified with 10% sodium hydroxide solution. The organics were re-extracted into ethyl acetate/ether (1:1). Evaporation of this organic solution after washing and drying left 5.4 g of a crude solid. TLC analysis of this free base showed an impurity which hindered the formation of crystalline maleate salt. Recrystalline of the free base from ethyl acetate removed this impurity and the maleate salt was formed by dissolving the recrystallized free base in ethyl acetate and treating it with an excess ethereal maleic acid. Recrystallization of the precipitate from methanol/acetone/ether gave a crystalline solid (1.7 g), m.p. 124°-126° C.

ANALYSIS: Calculated for $C_{17}H_{20}N_2O_3S \cdot C_4H_4O_4$: 56.24%C, 5.39%H, 6.25%N. Found: 56.12%C, 5.36%H, 6.20%N.

EXAMPLE 26

1-[(1,1-Dimethylethyl)amino]-3-[3-(thieno[2,3-d]isoxazol-3-yl)phenoxy]-2-propanol maleate To a solution containing 3.2 g of epibromohydrin in 8 ml of dimethylformamide were added 3.0 g of 3-(3-hydroxyphenyl)thieno[2,3-d]isoxazole and 3.2 g of potassium carbonate. The solution was stirred under nitrogen at 70°–80° C. for six hours and then quenched with water. The organics were extracted into ether, and the ether solution was washed with water and dried over anhydrous magnesium sulfate. Evaporation of the ether left 4 g of an oil which was then stirred with 13 ml of ethanol and 5 ml of tert-butylamine at reflux for four hours under nitrogen. Concentration of the reaction mixture in vacuo left a residue which was taken up in 200 ml of ether. This solution was shaken with 10% hydrochloric acid and the acidic aqueous phase was basified with 10% sodium hydroxide solution, followed by extraction (3x) with ethyl acetate/ether (1:1). The combined organic solution was washed with water, dried and concentrated in vacuo to give 2.7 g of a crystalline solid. This solid was dissolved in methanol and treated with an excess of maleic acid in methanol. Concentration of the methanol solution left a crystalline solid which was washed repeatedly with ether to remove excess maleic acid. Recrystalline of the crude maleate salt from methanol/acetone/ether gave a crystalline solid, m.p. 162°–163.5° C.

ANALYSIS: Calculated for $C_{18}H_{22}N_2O_3S \cdot C_4H_4O_4$: 57.13%C, 5.67%H, 6.06%N. Found: 56.91%C, 5.79%H, 5.99%N.

EXAMPLE 27

1-[[2-(3,4-Dimethyoxyphenyl)ethyl]amino]-3-[3-[thieno[2,3-d]isoxazol-3-yl]-phenoxy]-2-propanol hydrochloride A mixture of 3-(3-hydroxyphenyl)thieno[2,3-d]isoxazole (4.0 g), epibromohydrin (3.5 g) and potassium carbonate (4 g) was stirred in 15 ml of dimethylformamide at 70°–80° C. for six hours under nitrogen. The reaction mixture was then quenched with water, the organics were extracted into ethyl acetate, and the ethyl acetate solution was washed three times with water and dried over anhydrous magnesium sulfate. Evaporation of the ethyl acetate solution left 5.4 g of an oil which was passed through a silica gel column packed in hexane. Elution with dichloromethane gave 4.1 g of a crystalline solid, which was taken up in 15 ml of ethanol and heated to relux with 3.26 g of beta-(3,4-dimethoxyphenyl)ethylamine for two hours under nitrogen. The reaction mixture was concentrated to a residue and the residue was taken up in 250 ml of ether/ethyl acetate (1:1). This organic solution was shaken with 10% hydrochloric acid and discarded. The aqueous acidic phase was basified with 10% sodium hydroxide and extracted three times with ether/ethyl acetate (1:1). Washing, drying and evaporation of this organic solution left 6 g of an oil, which was passed through a silica gel column packed in dichloromethane. Elution with 50% methanol/dichloromethane gave 3.5 g of an oil which was converted to the hydrochloride salt by dissolving the oil in acetone/ether (1:1) and adding an excess of ethereal hydrochloride. After recrystallizing this sample (2.2 g) from methanol/acetone/ether, it was combined with 1.0 g of another sample similarly prepared. The combined sample was recrystallized from methanol/acetone/ether, m.p. 187°–190° C.

ANALYSIS: Calculated for $C_{24}H_{26}N_2O_5S \cdot HCl$: 58.71%C, 5.54%H, 5.71%N. Found: 58.59%C, 5.54%H, 5.64%N.

EXAMPLE 28

(3-Bromothien-2-yl) (3-methoxyphenyl)methanone hydrazone

A mixture of (3-bromothien-2-yl) (3-methoxyphenyl)methanone (10.0 g), hydrazine hydrate (10 ml, above 99% purity), and 75 ml of ethylene glycol was heated at 130° C. for three hours. The reaction mixture was then quenched with water and extracted with ether. The ether solution was washed three times with water and dried over anhydrous magnesium sulfate. The ether was then evaporated to give 5.5 g of an oil. This was then column chromatographed on a silica gel column packed in hexane using 15% ether/hexane as an eluent. The solid from the column was then recrystallized from ether/hexane.

ANALYSIS: Calculated for $C_{12}H_{11}BrN_2OS$: 46.31%C, 3.56%H, 9.00%N. Found: 46.65%C, 3.68%H, 9.03%N.

EXAMPLE 29

(3-Bromothien-2-yl) (4-methoxyphenyl)methanone

A solution of phenyllithium (67 ml, 1.65M in ether/benzene) was added dropwise to a solution of 16.3 g of 3-bromothiophene in 100 ml of dry ether at room temperature under nitrogen. After the addition, the solution was stirred overnight under nitrogen. The resultant solution was then added dropwise to a solution of p-methoxybenzoyl chloride (20.5 g) in 80 ml of tetrahydrofuran at −70° C. over two hours and stirring was further continued for two hours at the same temperature. The reaction was then quenched with water, the organics were extracted into ether, and the ether phase was washed with 10% aqueous sodium hydroxide solution and water and dried over anhydrous magnesium sulfate. Upon evaporation of the solvent, oily liquid was obtained which was chromatographed by high performance liquid chromatography with 5% ethyl acetate/hexane used as an eluent. Appropriate fractions were combined and evaporated to give crystals which were recrystallized from ether/hexane (yield 11.9 g).

ANALYSIS: Calculated for $C_{12}H_9O_2BrS$: 48.50%C, 3.05%H. Found: 48.20%C, 3.00%H.

EXAMPLE 30

(3-Bromothien-2-yl) (4-methoxyphenyl)methanone oxime

A mixture of (3-bromothien-2-yl) (4-methoxyphenyl)methanone (2.5 g) and hydroxylamine hydrochloride (1.5 g) and 15 ml of pyridine was stirred at room temperature overnight and then heated at 100°–115° C. for 4 hours. A thin layer chromatography analysis showed the reaction to be complete. The mixture was quenched with water and extracted with ether. The ether phase was washed with 3N hydrochloric acid and water and dried over anhydrous magnesium sulfate. Upon evaporation of the ether, an oil was obtained which crystallized upon standing overnight. The solid was recrystallized from ether/pentane to give a pure crystalline product (2.39 g, m.p. 110°–115° C.).

ANALYSIS: Calculated for $C_{12}H_{10}BrNO_2S$: 46.175C, 3.28%H, 4.49%N. Found: 46.19%C, 3.285H, 4.48%N.

EXAMPLE 31

3-(4-Methoxyphenyl)thieno[2,3-d]isoxazole

A solution of 40 g of (3-bromothien-2-yl) (4-methoxyphenyl)methanone oxime in 700 ml of ethoxyethanol was treated with 16 g of potassium hydroxide in 100 ml of water. After 15 minutes at 105°, 0.8 g of CuCl was added and the mixture was refluxed at 107°–108° for 1 hour during which a dark color developed and the starting material disappeared completely.

The mixture was poured onto 1000 ml of water (cold) and extracted with 100 ml of ether. The solution was filtered with the aid of Celite to remove copper salts and the clear layers were separated.

The aqueous phase was extracted three times with 400 ml of ether. The combined ether solution was washed with water (4×500 ml) and dried over anhydrous magnesium sulfate.

Evaporation of the solvent yielded a solid which was triturated with 300 ml of 15% ether/hexane and filtered. This material was used for the subsequent synthesis.

EXAMPLE 32

3-(4-Hydroxyphenyl)thieno[2,3-d]isoxazole

A solution of 6.94 g of 3-(4-methoxyphenyl)-thieno[2,3-d]isoxazole in 40 ml of dichloromethane was treated dropwise with 1M solution of boron tribromide in dichloromethane. A precipitate appeared after a few minutes. The suspension was stirred overnight and thereafter quenched with 10% hydrochloric acid. Extraction with ether followed by washing and drying gave a solid which was found to be contaminated with 5% of the starting material. The crude product was fed to an alumina column packed in ether.

Elution with ether removed the starting material, and further elution with 20% methanol/ether afforded 4.2 g of prisms which were analytically pure. Alternatively the product could be purified by recrystallization from acetone/hexane, m.p. 174.5°–176° C.

ANALYSIS: Calculated for $C_{11}H_7NO_2S$: 60.81%C, 3.25%H, 6.45%N. Found: 60.97%C, 3.42%H, 6.50%N.

EXAMPLE 33

1-[(1-Methylethyl)amino]-3-[4-(thieno[3,2-d]isoxazole-3-yl)phenoxy]-2-propanol maleate A mixture of 3 g of 3-(4-epoxymethoxyphenyl)-thieno[2,3-d]isoxazole (prepared from epibromohydrin and 3-(4-hydroxyphenyl)thieno[2,3-d]isoxazole in substantially the same manner as Example 5), 5 ml of absolute ethanol and 5 ml of isopropylamine was refluxed for three hours. The excess amine and ethanol were removed under a reduced pressure, leaving a residue. The crude product was extracted into 400 ml of ethyl acetate/ether (1:1) and shaken with ice-cold (10%) hydrochloric acid. The aqueous solution was separated and basified with concentrated $NH_3$ to liberate the product. Extraction with ethyl acetate/ether (1:1) followed by washing and drying yielded a colorless solid weighing 2.8 g. The free base was converted to crystalline maleate in ethyl acetate/ether and recrystallized from methanol/ether to afford plates, m.p. 153°–155° C.

ANALYSIS: Calculated for $C_{19}H_{20}N_2O_3S.C_4H_4O_4$: 56.24%C, 5.39%H, 6.25%N. Found: 56.29%C, 5.47%H, 6.17%N.

EXAMPLE 34

1-[(1,1-Dimethylethyl)amino]-3-[4-(thieno[3,2-d]isoxazol-3-yl)phenoxy]-2-propanol A mixture of 3.0 g of 3-(4-hydroxyphenyl)thieno[2,3-d]isoxazole, 2.5 g of epibromohydrin, 3.2 g of potassium carbonate and 8 ml of dimethylformamide was stirred at 70°–80° for 6 hours. The solution was cooled and diluted with 300 ml of water and the precipitate was filtered and dried at 50° in vacuum overnight.

The crude epoxide was added to a solution prepared from 10 ml of ethanol and 5 ml of tertiary-butylamine. Refluxing was maintained for 16 hours. The cooled solution was concentrated in vacuo to remove the solvent and the excess amine, and the residue was diluted with 250 ml of ether. Extraction of the ethereal solution with 10% hydrochloric acid followed by basification of the acidic solution with 10% sodium hydroxide solution yielded an oil which was taken up in ether. The combined ethereal solution was washed twice with water, dried over anhydrous magnesium sulfate and concentrated in vacuo to give an oil which crystallized on cooling. Recrystallization of the crude product from acetone/hexane gave 2.87 g of crystals, m.p. 117.5°–118.5° C.

ANALYSIS: Calculated for $C_{18}H_{22}N_2O_3S$: 62.40%C, 6.40%H, 8.09%N. Found: 62.23%C, 6.40%H, 7.93%N.

EXAMPLE 35

(3-Bromothien-2-yl) (4-methoxyphenyl)methanone hydrazone

A mixture prepared form 18 g of (3-bromothien-2-yl) (4-methoxyphenyl)methanone, 12 ml of hydrazine hydrate (99%) and 120 ml of ethylene glycol was stirred at 120° for 2 hours. Thereafter, the mixture was cooled and diluted with 1000 g of ice water and quickly extracted with ether (3×500 ml). The combined ether solution was washed four times with water to remove unreacted hydrazine and dried over anhydrous magnesium sulfate overnight.

Removal of ether under reduced pressure gave a thick oil which was essentially homogeneous by thin layer chromatography. The material was further purified by column chromatography over silica. Elution with dichloromethane gave 14 g of an oil.

ANALYSIS: Calculated for $C_{12}H_{11}BrN_2OS$: 46.30%C, 3.56%H, 9.00%N. Found: 46.20%C, 3.48%H, 8.70%N.

EXAMPLE 36

3-(4-Methoxyphenyl)-1H-thieno[3,2-c]pyrazole

A solution of 1.0 g of (3-bromothien-2-yl) (4-methoxyphenyl)methanone hydrazone in 60 ml of ethoxyethanol was treated with an alkaline solution prepared by dissolving 6.0 g of 85% potassium hydroxide pellets in 20 ml of water. The resultant solution was stirred at 105°–110° for 30 minutes and to it under nitrogen was added 250 ml of finely powdered cuprous chloride. The darkened mixture was maintained at 105°–110° C. for an additional 90 minutes and quenched with water. The organic materials were extracted exhaustively with ethyl acetate/ether (1:1) and the combined organic solution was washed (four times) with water and dried. Evaporation of the solvents afforded a thick oil which was purified by passage through an alumina column. Elution with ether removed most of the dark impurities and further elution with 5% methanol/ether gave 5.2 g of an oil which solidified on scratching, m.p. 143°–144° C. For analysis, a small sample was recrystallized from ether/hexane without any change in the melting range.

ANALYSIS: Calculated for $C_{12}H_{10}N_2OS$: 62.58%C, 4.38%H, 12.17%N. Found: 63.01%C, 4.51%H, 12.37%N.

EXAMPLE 37

1-[[2-(3,4-Dimethoxyphenyl)ethyl]amino]-3-[2-[1H-thieno[3,2-c]pyrazol-3-yl]phenoxy]-2-propanol fumarate A solution of 3-[2-epoxymethoxyphenyl]-1-methyl-1H-thieno[3,2-c]pyrazole (4.0 g) and 2.8 g of beta-(3,4-dimethoxyphenyl)ethylamine in 15 ml of ethanol was stirred at reflux under nitrogen for 20 hours. The reaction vessel was cooled to room temperature and quenched with water. The product was taken up into a 1:1 ether/ethyl acetate solution, washed and dried. Evaporation of solvents afforded a crude oil which was purified by HPLC using 2:1 ethyl acetate/methanol as the eluent. The resultant oily compound was dissolved in ether and treated with ethereal fumaric acid to give a low melting salt which was purified by recrystallization with ethanol/ether, mp 80°–83° C. The yield was 2.8 g.

ANALYSIS: Calculated for $C_{25}H_{29}N_3O_4S \cdot C_4H_4O_4$: 59.68%C, 5.70%H, 7.20%N. Found: 59.31%C, 5.98%H, 6.97%N.

EXAMPLE 38

1-[[2-[(2-Methoxy)phenoxy]ethyl]amino]-3-[2-[1-methyl-1H-thieno[3,2-c]pyrazol-3-yl]phenoxy]-2-propanol hemifumarate A mixture of 3-[2-epoxymethoxyphenyl]-1-methyl-1H-thieno[3,2-c]pyrazole (4.76 g) and 2-[2-(methoxy)phenoxy]ethylamine (3 g) in 15 ml of ethanol was refluxed for 16 hours. The reaction was quenched with water and the organics were extracted into a 1:1 ether/ethyl acetate solution. Washing with water, drying with anhydrous magnesium sulfate and evaporation of solvents resulted in an oil which was purified by HPLC using 8:1 dichloromethane/methanol as the eluent. The purified oil was dissolved in ether and converted to the fumarate salt. Recrystallization from ethanol-ether afforded a solid having a melting point of 132°–135° C. The yield was 2.9 g.

ANALYSIS: Calculated for $C_{24}H_{27}N_3O_4S \cdot C_4H_4O_4$: 61.04%C, 5.71%H, 8.21%N. Found: 60.78%C, 5.82%H, 8.25%N.

EXAMPLE 39

1-[[(1Methyl-2-phenoxy)ethyl]amino]-3-[2-[1H-thieno[3,2-c]pyrazol-3-yl]phenoxy]-2-propanol maleate A mixture of 3-[2-epoxymethoxyphenyl]-1-methyl-1H-thieno[3,2-c]pyrazole (5 g) and (1-methyl-2-phenoxy)ethylamine (2.9 g) was refluxed in 20 ml of ethanol for 19 hours. The reaction was quenched with water and the organics were extracted into 1:1 ether/ethyl acetate solution. Washing with water, drying with anhydrous magnesium sulfate and evaporation of solvents resulted in a thick oil which was purified by HPLC using 6:1 dichloromethane/methanol as the eluent. The purified oil was dissolved in ether and converted to the maleate salt. Recrystallization was conducted from ethanol (mp 132°–134° C). The yield was 3.3 g.

ANALYSIS: Calculated for $C_{24}H_{27}N_3O_3S \cdot C_4H_4O_4$: 60.74%C, 5.64%H, 7.59%N. Found: 60.63%C, 5.65%H, 7.49%N.

EXAMPLE 40

1-[[[2-[(2-Methoxy)phenoxy]-1-methyl]ethyl]amino]-3-[2-[1-methyl-1H-thieno[3,2-c]pyrazol-3-yl]phenoxy]-2-propanol maleate A mixture of 3-[2-epoxymethoxyphenyl]-1-methyl-1H-thieno[3,2-c]pyrazole (4.3 g) and 2-(2-methoxy)-phenoxy-1-methylethylamine (3 g) in 20 ml of ethanol was refluxed for 19 hours. The reaction was quenched with water and the organics were extracted into a 1:1 ether/ethyl acetate solution. Washing with water, drying with anhydrous magnesium sulfate, and evaporation of solvents resulted in a thick oil which was purified by HPLC using 4:1 dichloromethane/methanol as the eluent. The purified oil was dissolved in ether and converted to the maleate salt (mp 130°–132° C). The yield was 3.1 g.

ANALYSIS: Calculated for $C_{25}H_{29}N_3O_4S \cdot C_4H_4O_4$: 59.67%C, 5.69%H, 7.20%N. Found: 59.62%C, 5.93%H, 7.22%N.

EXAMPLE 41

3-(3-Epoxymethoxyphenyl)thieno[2,3-d]isoxazole

A mixture of 28 g of 3-(3-hydroxyphenyl)thieno[2,3-d]isoxazole, 23 g of epibromohydrin and 30 g of milled potassium carbonate in 40 ml of dimethylformamide and 40 ml of acetonitrile was stirred under nitrogen at 90°–100° C. until completion of reaction. The reaction was complete after 4 hours and allowed to cool to room temperature. Quenching with water (400 ml), extracting with 50/50 ether/ethyl acetate soluiton (3×400 ml), and washing with water (2×400 ml) were conducted. The organics were dried over anhydrous magnesium sulfate and the solvents were evaporated to give an oil. The oil was purified by HPLC (4:1 hexane/ethyl acetate) to yield 23.3 g of a solid with a melting point of 88°–90° C.

ANALYSIS: Calculated for $C_{14}H_{11}NO_3S$: 61.53%C, 4.06%H, 5.12%N. Found: 61.48%C, 4.02%H, 5.07%N.

EXAMPLE 42

3-(3-Methoxyphenyl)-1-methyl-1H-thieno[3,2-c]pyrazole

A mixture of 20 g of (3-bromothien-2-yl) (3-methoxyphenyl)methanone and 17 g of methyl hydrazine in 134 ml of ethylene glycol was stirred under nitrogen at 120°–130° C. The reaction was complete in 2.5 hours. The product was allowed to cool to room temperature, and thereafter quenched with water (200 ml) and extracted with ether (4×200 ml). The organics were dried over anhydrous magnesium sulfate and the solvents were evaporated to give an oil. The oil was purified by HPLC (3:1 hexane/ethyl acetate). This yielded 9 g of a solid which was recrystallized from ether to give 8.2 g of crystals, mp 99°–101° C.

ANALYSIS: Calculated for $C_{13}H_{12}N_2OS$: 63.90%C, 4.95%H, 11.47%N. Found: 63.63%C, 5.03%H, 11.52%N.

EXAMPLE 43

1-[1-Methylethylamino]-3-[3-[1-methyl-1H-thieno[3,2-c]pyrazol-3-yl]phenoxy]-2-propanol A mixture prepared from 29 g of 3-[3-epoxymethoxyphenyl]-1-methyl-1H-thieno[3,2-c]pyrazole and 1.4 g of isopropylamine in 5 ml of ethanol was refluxed until completion of reaction (2 hours). The reaction product was allowed to cool to room temperature and then concentrated to an oil. The oil was diluted in benzene and the solvent was evaporated to give a solid which was purified by HPLC using 9:1 dichloromethane/methanol as the eluent. Recrystallization from ethanol/ether afforded a solid with a melting point of 106°–108° C. The yield was 1.1 g.

ANALYSIS: Calculated for $C_{18}H_{23}N_3O_2S$: 62.68%C, 6.71%H, 12.16%N. Found: 62.10%C, 6.60%H, 12.07%N.

We claim:

1. A compound of formula

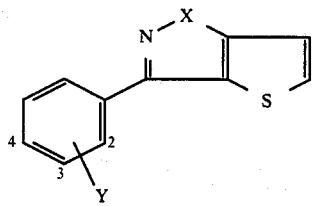

where X is O or NR, R being hydrogen or loweralkyl; and Y is —OCH$_3$, —OH or

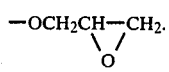

2. The compound as defined in claim 1, where X is oxygen.

3. The compound as defined in claim 2, where Y is —OCH$_3$.

4. The compound as defined in claim 2, where Y is —OH.

5. The compound as defined in claim 2, where Y is

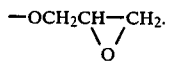

6. The compound as defined in claim 3, where the —OCH$_3$ group is in the 2-position of the phenyl ring.

7. The compound as defined in claim 3, where the —OCH$_3$ group is in the 3-position of the phenyl ring.

8. The compound as defined in claim 3, where the —OCH$_3$ group is in the 4-position of the phenyl ring.

9. The compound as defined in claim 4, where the —OH group is in the 2-position of the phenyl ring.

10. The compound as defined in claim 4, where the —OH group is in the 3-position of the phenyl ring.

11. The compound as defined in claim 4, where the —OH group is in the 4-position of the phenyl ring.

12. The compound as defined in claim 5, where the

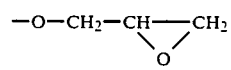

group is in the 2-position of the phenyl ring.

13. The compound as defined in claim 5, where the

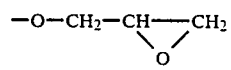

group is in the 3-position of the phenyl ring.

14. The compound as defined in claim 5, where the

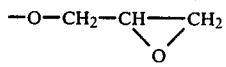

group is in the 4-position of the phenyl ring.

15. The compound as defined in claim 1, where X is NR.

16. The compound as defined in claim 15, where R is CH$_3$.

17. The compound as defined in claim 16, where Y is —OCH$_3$.

18. The compound as defined in claim 16, where Y is —OH.

19. The compound as defined in claim 16, where Y is

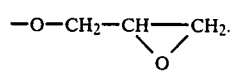

20. The compound as defined in claim 17, where the —OCH$_3$ group is in the 2-position of the phenyl ring.

21. The compound as defined in claim 17, where the —OCH$_3$ group is in the 3-position of the phenyl ring.

22. The compound as defined in claim 17, where the —OCH$_3$ group is in the 4-position of the phenyl ring.

23. The compound as defined in claim 18, where the —OH group is in the 2-position of the phenyl ring.

24. The compound as defined in claim 18, where the —OH group is in the 3-position of the phenyl ring.

25. The compound as defined in claim 18, where the —OH group is in the 4-position of the phenyl ring.

26. The compound as defined in claim 19, where the

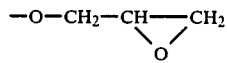

group is in the 2-position of the phenyl ring.

27. The compound as defined in claim 19, where the

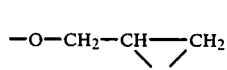

group in the 3-position of the phenyl ring.

28. The compound as defined in claim 19, where the

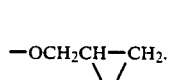

group is in the 4-position of the phenyl ring.

29. The compound as defined in claim 15, where R is H.

30. The compound as defined in claim 29, where Y is —OCH$_3$.

31. The compound as defined in claim 29, where Y is —OH.

32. The compound as defined in claim 29, where Y is

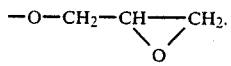

33. The compound as defined in claim 30, where the —OCH$_3$ group is in the 2-position of the phenyl ring.

34. The compound as defined in claim 30, where the —OCH$_3$ group is in the 3-position of the phenyl ring.

35. The compound as defined in claim 30, where the —OCH$_3$ group is i the 4-position of the phenyl ring.

36. The compound as defined in claim 31, where the —OH group is in the 2-position of the phenyl ring.

37. The compound as defined in claim 31, where the —OH group is in the 3-position of the phenyl ring.

38. The compound as defined in claim 31, where the —OH group is in the 4-position of the phenyl ring.

39. The compound as defined in claim 32, where the

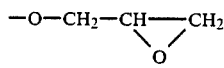

group is in the 2-position of the phenyl ring.

40. The compound as defined in claim 32, where the

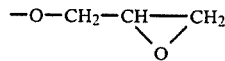

group is in the 3-position of the phenyl ring.

41. The compound as defined in claim 32, where the

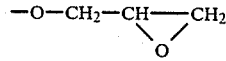

group is in the 4-position of the phenyl ring.

42. A compound of the formula

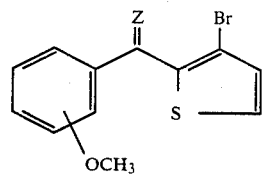

where Z is O, NOH or NNHR$_4$, R$_4$ being hydrogen or loweralkyl.

43. The compound as defined in claim 42, where Z is oxygen.

44. The compound as defined in claim 43, where the methoxy group is in the 2-position of the phenyl ring.

45. The compound as defined in claim 43, where the methoxy group is in the 3-position of the phenyl ring.

46. The compound as defined in claim 43, where the methoxy group is in the 4-position of the phenyl ring.

47. The compound as defined in claim 43, where Z is NOH.

48. The compound as defined in claim 47, where the methoxy group is in the 2-position of the phenyl ring.

49. The compound as defined in claim 47, where the methoxy group is in the 3-position of the phenyl ring.

50. The compound as defined in claim 47, where the methoxy group is in the 4-position of the phenyl ring.

51. The compound as defined in claim 47, where Z is NNH$_2$.

52. The compound is defined in claim 47, where the methoxy group is in the 2-position of the phenyl ring.

53. The compound as defined in claim 47, where the methoxy group is in the 3-position of the phenyl ring.

54. The compound as defined in claim 47, where the methoxy group is in the 4-position of the phenyl ring.

55. The compound as defined in claim 42, where Z is NNHCH$_3$.

56. The compound as defined in claim 55, where the methoxy group is in the 2-position of the phenyl ring.

57. The compound as defined in claim 55, where the methoxy group is in the 3-position of the phenyl ring.

58. The compound as defined in claim 55, where the methoxy group is in the 4-position of the phenyl ring.

* * * * *